United States Patent [19]

Sones et al.

[11] Patent Number: 4,885,761
[45] Date of Patent: Dec. 5, 1989

[54] GRAVITY ACTUATED X-RAY SCANNER

[75] Inventors: Richard A. Sones, Cleveland Heights; Mike M. Tesic, Cleveland; James F. Vidmar, Willoughby Hills, all of Ohio

[73] Assignee: Picker International, Inc., Cleveland, Ohio

[21] Appl. No.: 863,328

[22] Filed: May 15, 1986

[51] Int. Cl.$^4$ ............................................. H05G 1/02
[52] U.S. Cl. ............................... 378/197; 378/195; 378/196; 378/198; 250/360.1; 250/363.05
[58] Field of Search ................. 378/10, 11, 15, 21–27, 378/39, 40, 146, 195–198; 250/360.1, 363.05

[56] References Cited

U.S. PATENT DOCUMENTS

| | | | |
|---|---|---|---|
| 1,233,122 | 7/1917 | Pohl | 378/27 |
| 2,167,115 | 7/1939 | Kieffer | 378/24 |
| 2,235,144 | 3/1941 | Colcher | 378/26 |
| 2,493,161 | 1/1950 | Nemet | 378/197 |
| 3,456,114 | 7/1969 | Gray | 378/197 |
| 4,179,100 | 12/1979 | Sashin et al. | 378/22 |
| 4,187,429 | 2/1980 | Tomita et al. | 378/4 |
| 4,213,050 | 7/1980 | Meek | 378/26 |
| 4,426,715 | 1/1984 | Baer et al. | 378/4 |
| 4,658,408 | 4/1987 | Amor et al. | 378/4 |

FOREIGN PATENT DOCUMENTS 1118928 12/1961 Fed. Rep. of Germany ........ 378/26

Primary Examiner—Craig E. Church
Assistant Examiner—John C. Freeman
Attorney, Agent, or Firm—Watts, Hoffman, Fisher & Heinke Co.

[57] ABSTRACT

A digital scan projection radiography system is disclosed which is particularly adapted for the rigors of portable deployment. The system scans by gravity. A cam mechanism is employed which raises the pivot of a pivotally suspended scanner assembly including source, detector and other components to render gravitational potential energy of the scanner assembly approximately linear with respect to angular scanning displacement. This feature enables limiting scanning angular velocity to an approximately constant value with the aid of only a friction brake. The feature also causes the detector scanning path to more closely approximate a linear path than an arcuate path which would result from simple pivotal pendulum scanning.

41 Claims, 10 Drawing Sheets

GRAVITY ACTUATED X-RAY SCANNER

TECHNICAL FIELD

This invention relates to the field of medical diagnostics, and more particularly to an improved method and apparatus especially suited for use in the environment of scan projection digital radiography for facilitating providing scanning motion and for the facilitation of control of scanning speed and of scanning path.

BACKGROUND ART

In a conventional radiography system, an x-ray source is actuated to direct a divergent area beam of x-rays through a patient. A cassette containing an x-ray sensitive phosphor screen and light and x-ray sensitive film is positioned in the x-ray path on the side of the patient opposite the source. Radiation passing through the patient's body is attenuated in varying degrees in accordance with the various types of tissue through which the x-rays pass. The attenuated x-rays from the patient emerge in a pattern, and strike the phosphor screen, which in turn exposes the film. The x-ray film is processed to yield a visible image which can be interpreted by a radiologist as defining internal body structure and/or condition of the patient.

More recently, digital radiography techniques have been developed. In digital radiography, the source directs x-radiation through a patient's body to a detector in the beam path beyond the patient. The detector, by use of appropriate sensor means, responds to incident radiation to produce analog signals representing the sensed radiation image, which signals are converted to digital information and fed to a digital data processing unit. The data processing unit records, and/or processes and enhances the digital data. A display unit responds to the appropriate digital data representing the image to convert the digital information back into analog form and produce a visual display of the patient's internal body structure derived from the acquired image pattern of radiation emergent from the patient's body. The display system can be coupled directly to the digital data processing unit for substantially real time imaging, or can be fed stored digital data from digital storage means such as tapes or discs representing patient images from earlier studies.

Digital radiography includes radiographic techniques in which a thin spread beam of x-rays is used. In this technique, often called "scan (or slit) projection radiography" (SPR), a spread beam of x-rays is directed through a patient's body. The beam is scanned across the patient, or the patient is movably interposed between the beam x-ray source and an array of individual cellular detector segments. In such an embodiment, relative movement is effected between the source-detector arrangement and the patient's body, keeping the detector aligned with the beam, such that a large area of the patient's body is scanned by the beam of x-rays. Each of the detector segments produces analog signals indicating characteristics of the received x-rays. These analog signals are digitized and fed to the data processing unit which operates on the data in a predetermined fashion to actuate the display apparatus to produce a display image representing the internal structure and/or condition of the patient's body.

One of the general advantages of digital radiography is that the digital image information generated from the emergent radiation pattern and incident on the detector can be processed, more easily than analog data, in various ways to enhance certain aspects of the image, to make the image more readily intelligible and to display a wider range of anatomical attenuation differences.

Recent advances in digital radiography have given rise to techniques known as "energy subtraction" in which tissue specific images can be made, wherein the image of only a particular type of tissue, e.g., bone or soft tissue, dominates the picture. Such techniques are described in an article by Lehmann, L. A. et al.: "Generalized Image Combination In Dual KVP Digital Radiography", *Medical Physics*, 8: 659–667, 1981, which is expressly incorporated herein by reference.

It has been proposed in energy subtraction to utilize a particular type of dual energy detector assembly which can produce separate signals representing each of lower and higher x-ray energy incident on the detector. Such a detector assembly enables the practice of energy subtraction without the necessity for switching KVP x-ray output levels, or employing other means for periodically attenuating the x-ray beam, such as rapid interposition and removal of a filter to and from the x-ray path. Such a detector employs a dual layer of phosphor-detector elements wherein the phosphor material of a first, or front layer preferentially responds to energy of a relatively lower energy value. A second, or rear, detector layer preferentially responds to x-ray energy in a higher range. Such a detector, and its method of use, is described in U.S. patent application Ser. No. 444,605, filed Nov. 26, 1982 by Gary T. Barnes, which application is hereby expressly incorporated by reference. Such a detector is also described in corresponding published European patent application No. 83307157.4 published on Aug. 8, 1984 by Gary T. Barnes, also incorporated by reference.

A digital radiation SPR imaging system as generally described above is explained in the following publication: Tesic, M. M. et al., "Digital Radiography of The Chest: Design Features And Considerations For a Prototype Unit", *Radiology*, Vol. 148 No. 1, pages 259–264, July 1983, which publication is hereby expressly incorporated by reference.

It has been proposed to provide the scanning motion in slit projection radiographic systems by means of electromechanical servo-systems driven by controllable electric motors. In such systems, an encoder is utilized to provide a closed loop feedback system wherein motor performance is adjusted in accordance with the sensed location of the detector.

While slit projection radiographic systems of this type have been tested and found satisfactory for operation in permanent installations, such as in permanent doctors' offices and large hospitals, these systems are inordinately complex and bulky for convenient use in portable applications. Such portable applications can include mobile x-ray equipment for transport to a scene of traumatic injury, such as for use in connection with domestic trauma treatment centers, and in mobile military hospitals and first aid stations.

In such applications, it is particularly desirable that all equipment be as simple and reliable as possible, since repair capability may be inaccessible in the field. The equipment should be able to withstand repeated assembly and disassembly for transport. It must be capable of being "knocked down," in such disassembly, into relatively small components which can be carried by humans without the aid of mechanical lifting and transport equipment, such as where it would be desirable to load an x-ray system in pieces into a helicopter for quick transport to and reassembly at a site of need.

Needless to say, x-ray equipment designed for mobile application must be sufficiently rugged to resist damage or maladjustment resulting from vibration and other shock which normally occurs during transport of field equipment.

Another problem inherent in mobile x-ray equipment is that, often, the equipment is used where electric power is in limited supply and form. It is sometimes a problem to find sufficient electric power, or the needed frequency, phase and/or voltage, to actuate relatively heavy electromechanical components such as motors and other servo equipment used to drive prior art type radiographic scanning equipment.

The requirements of radiographic equipment used for initial evaluation of extensive traumatic injury often differ somewhat from the requirements for radiographic equipment used in permanent installations. Often, in mobile units such as military field hospitals, often called "MASH", the most important requirement for a radiographic system is to be able to reliably scan large areas of the human body very quickly, and to rapidly produce an image of reasonable quality illustrating gross traumatic injury caused by shrapnel, bullets and the like. Extremely high degrees of resolution are not as important where the injuries sought to be diagnosed are generally large and easy to identify, given an image of reasonable quality.

It is an object of this invention to provide a lightweight, rugged, reliable, simple, inexpensive, easily disassembled moderate resolution digital slit projection radiographic system capable of executing scanning at an approximately constant velocity, without the need for the application of electromechanical scanning power.

DISCLOSURE OF THE INVENTION

The above noted problems and disadvantages of the prior art are reduced or eliminated by provision of a radiographic imaging scanner system including a source for propagating penetrative radiation through a portion of a subject to emerge from the subject in a pattern defining internal subject structure and/or condition. A radiation detector is also employed, spaced from the source to accommodate a patient between the source and detector, and positioned to receive radiation constituting the pattern. Means is provided for mounting the detector for scanning movement along a path which defines a curved line lying substantially in a vertical plane. The system also includes interpretive means associated with the detector for producing an image representing the received radiation, and hence representing the pattern of radiation emergent from the patient.

The system comprises a digital slit scan projection imaging system. Such a system incorporates collimation means for shaping the radiation from the source into a relatively thin spread beam directed at the detector. The detector itself is associated with circuitry for producing a digital representation of the sensed radiation, which is subsequently converted to analog form for actual viewing.

In accordance with a more specific feature, the detector is mounted on structure which defines its motion. In this embodiment, the detector scanning motion is effected by gravitational force, and takes place independently of application of other types of power.

This embodiment thus can execute scanning motion without the necessity for the application of electrical power, eliminating the need for electrical servo-mechanisms and motors, and further eliminating the need for any type of electrical supply to power the scanning motion. This enhances simplicity and reliability of the system, and reduces cost.

In a more specific embodiment, means is provided for regulating the speed of detector motion, to maintain detector scanning at an approximately constant value over the extent of its scan. In accordance with this embodiment, the detector is mounted in an assembly consisting of other components of the system, including an arm which is pivotally mounted as a pendulum. As the detector moves downwardly, an elevating mechanism coupled to the assembly serves to alter the elevation of the pivot of the assembly as a function of detector motion. This is done in order to regulate the descent of the center of mass of the entire assembly to maintain the rate of change of gravitational potential energy of the center of mass of the entire assembly at an approximately constant level with respect to scanning motion angular displacement.

In a preferred embodiment, this elevating mechanism includes guide structure coupled between the assembly and other portions of the system to provide for movement of the center of mass of the assembly along a path having a vertical component. A cam, and lift means engaging the cam, are also provided such that, as the detector proceeds along its path of motion, the cam and lift mechanism cooperate to change the elevation of a portion of the assembly. The shape of the cam is chosen to tailor the variation in the location of the assembly portion, with respect to detector motion, to maintain the desired approximately constant gravitational potential energy change rate of the entire assembly with respect to detector displacement.

Additionally, a simple friction brake can be added to the system to cause scanner angular velocity to approximate a constant during detector movement.

Another advantage of the cam arrangement is that the elevation of the assembly as a function of detector downward motion also modifies the path of detector travel from an essentially arcuate form, which would result from simple pivotal mounting of the pendulum-supported detector, to a path which more closely approximates a linear one.

The accordance with a preferred embodiment, the cam is provided with a detent portion which can releasably hold the detector at a predetermined park position once the detector is manually positioned at that predetermined position, to await the initiation of a subsequent scan.

Other aspects of the present invention will become apparent from a study of the following specific description of a preferred embodiment, and from the drawings, in which:

BEST MODE FOR CARRYING OUT THE INVENTION

Figure 1:
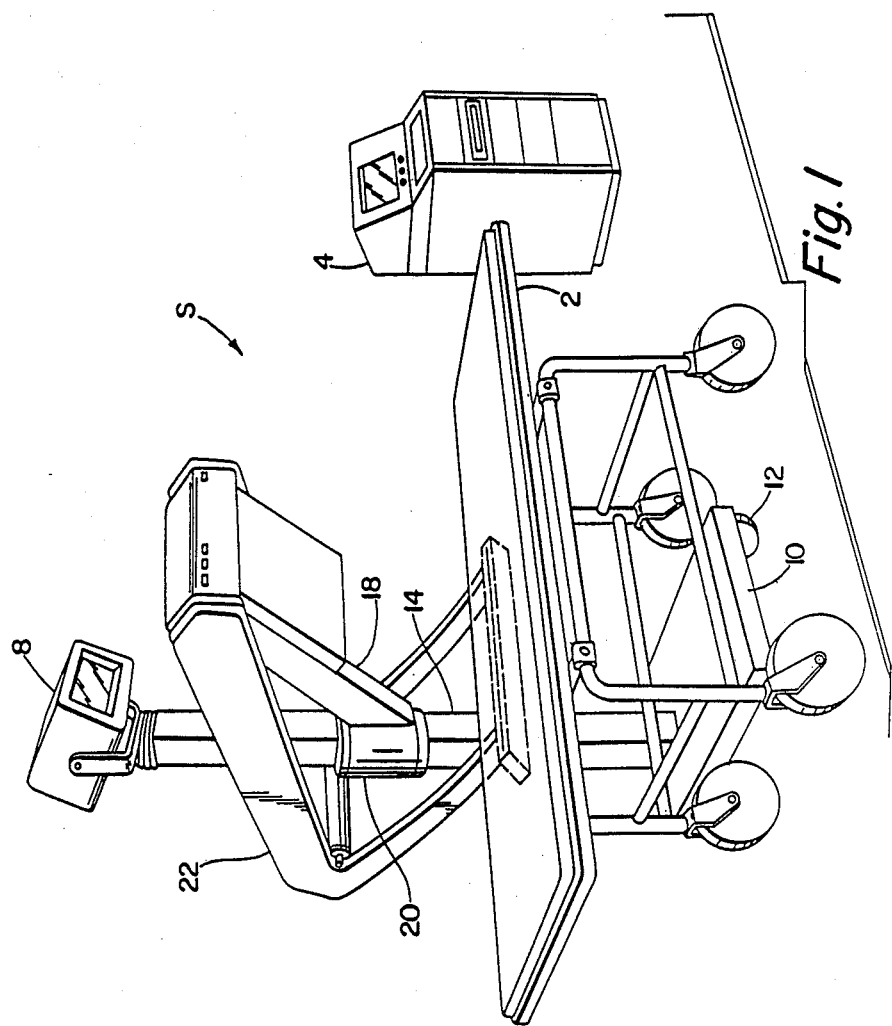
FIG. 1 is a perspective generalized drawing illustrating a system incorporating the present invention.
Figure 3:
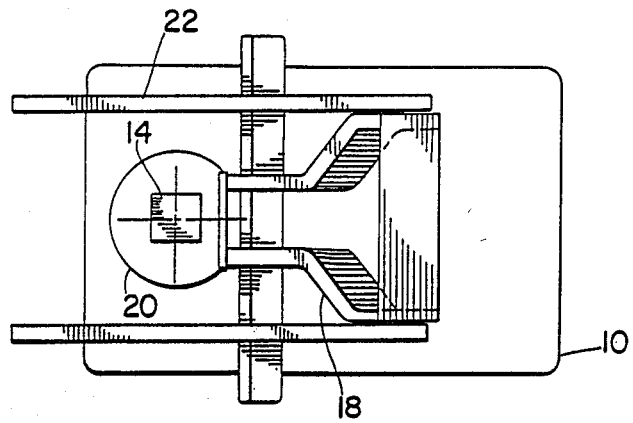
FIG. 3 is a plan view of the system illustrated in FIG. 1.

FIGS. 1-4 illustrate a slit projection type of digital radiography system S in which the present invention is incorporated. The system S pivot scans an x-ray spread beam approximately 1 millimeter in thickness, perpendicular to its thickness and generally about a horizontal axis across a large expanse of a patient's body, on a gurney such as at 2, and detects a pattern of x-rays emergent from the patient. Information represented by the detected x-rays is processed by processing circuitry in a console 4, and displayed to illustrate a representation of an image of the patient's internal body structure or condition, appearing on a monitor 8.

The system S includes a base 10 for supporting other components of the system. The base 10 is provided with mobility by the inclusion of wheels such as 12, and can also comprise adjustable leveling structure (not shown). The leveling structure for the base is useful when the system S is deployed in areas of uneven terrain.

The system also includes a substantially vertical tower member 14 which is fixed to the base 10 and extends in a generally vertical direction.

A support arm 18 is movably mounted on the tower member 14 by way of a collar structure 20. The collar structure 20 includes mechanism (not shown) of known type for facilitating vertical adjustment of the support arm 18 up and down on the tower member 14. This feature facilitates discretionary change in image magnification, accommodation of patient gurneys of varying height, and accommodation of stretcher patients.

Counterbalancing apparatus can be provided to compensate for the weight of the support arm 18 and the components mounted on it, as described below. Counterweighting apparatus is well known in the art. The counterbalancing apparatus prevents the system components from falling abruptly onto an operator or patient when a vertical adjustment of the support arm 18 is made. In addition, it permits an imaging height adjustment to be made by applying only a minimal vertical up or down force to the counterweighted assembly.

Figure 2:
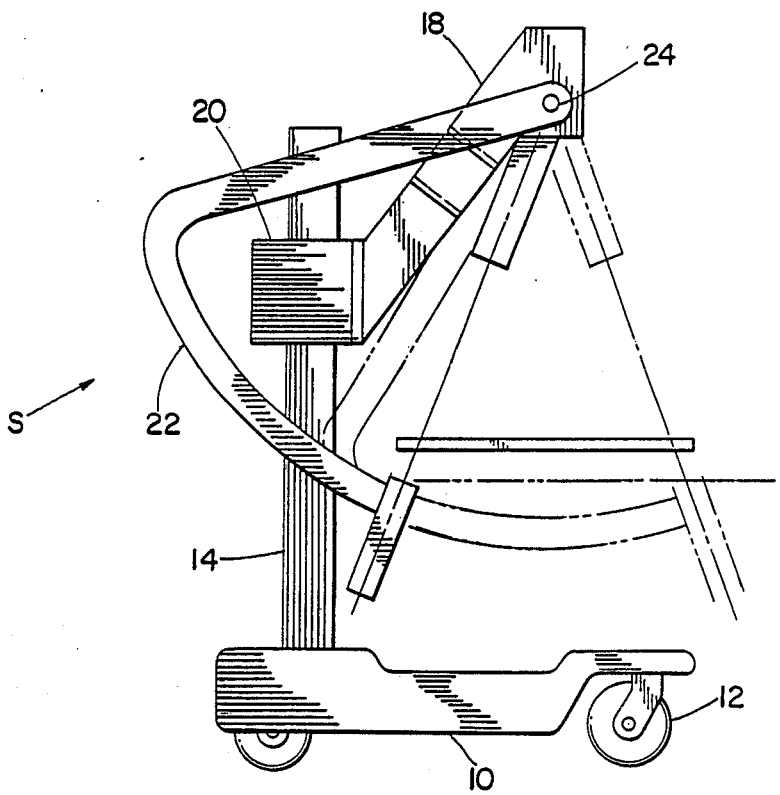
FIG. 2 is a side elevational view of a system incorporating the present invention.
Figure 4:
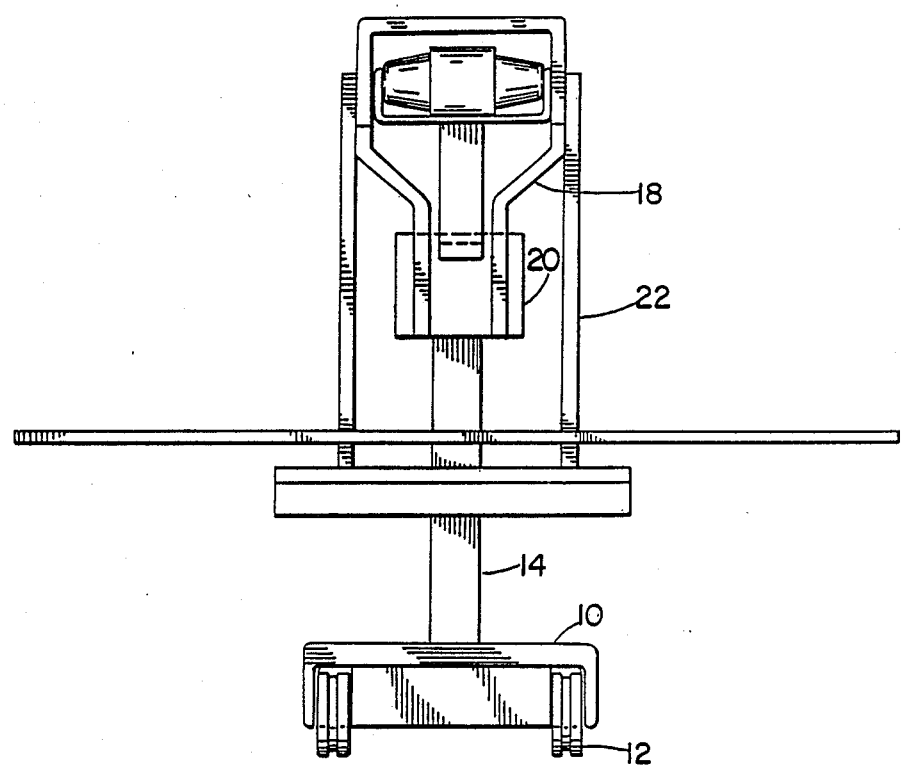
FIG. 4 is an end elevational view of the system illustrated in FIG. 1.

Many prior art counterweighting and motion limiting methods and apparatus may be used. Examples are weight-cable-pulley systems, hydraulic dashpot systems, and pnuematic systems.

a generally C-shaped pendulum arm 22 is journaled for rotation about a pivot shaft 24 which is attached near the outer end of the support arm 18. The pendulum arm 22 is free to rotate about the shaft 24, whose axis extends in a substantially horizontal direction. FIG. 2 illustrates in phantom a range of motion of which the pendulum arm is capable.

Figure 5:
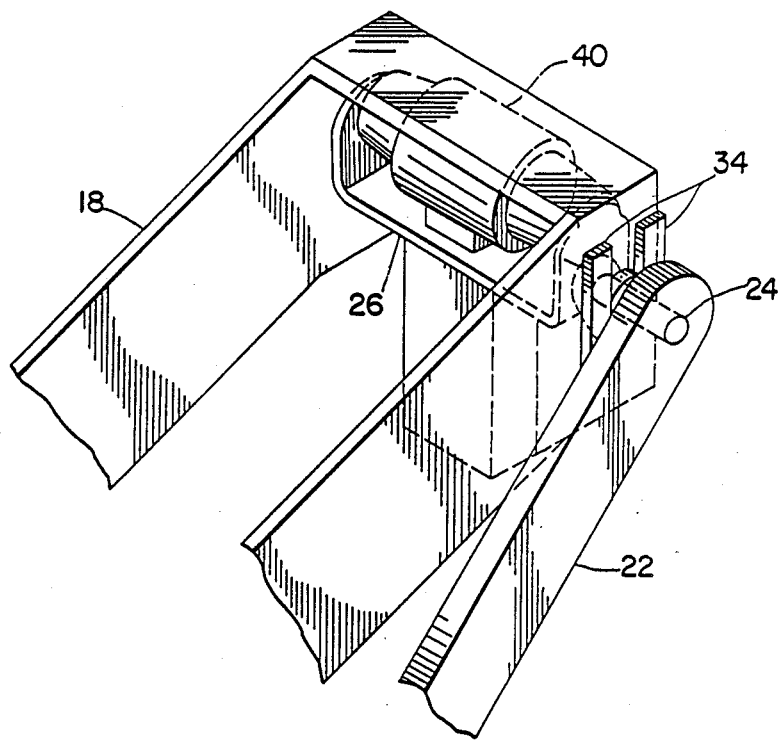
FIG. 5 is a detail drawing illustrating a portion of the system shown in FIGS. 1-4.

Coupled between the pendulum arm and the support arm 18 is a mechanism for regulating the velocity of the pivotal movement of the pendulum arm 22 about the shaft 24. This mechanism is illustrated in detail in FIGS. 5 and 6.

Figure 6:
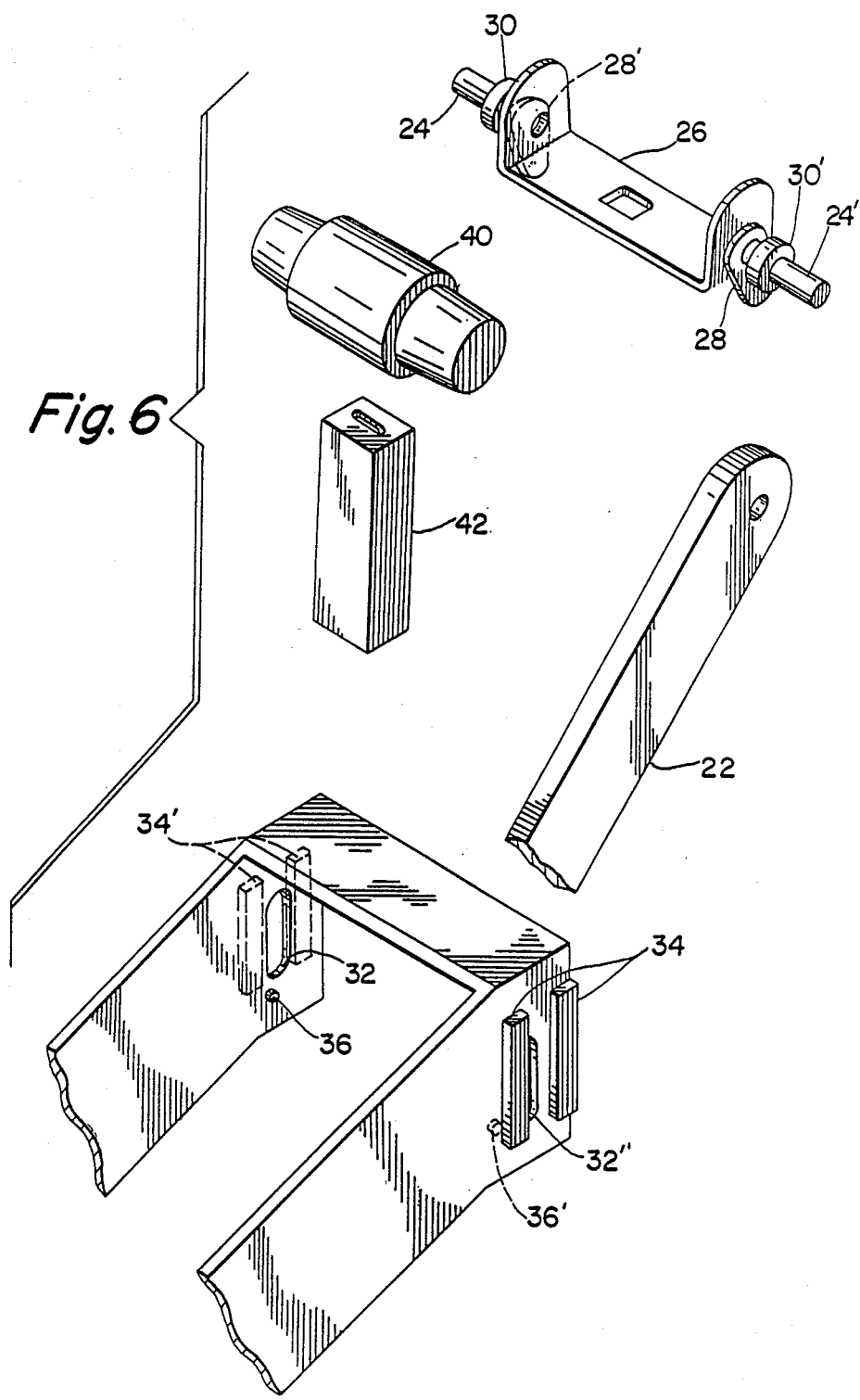
FIG. 6 is an exploded view illustrating a portion of the system shown in FIG. 5.

FIG. 6 illustrates in exploded format the pendulum arm 22 and two pivot shaft portions 24, 24'. Coupled to the pivot shaft portions for rotation with the pendulum arm 22 is an x-ray tube support 26. Also coupled to the pivot shaft portions for rotation therewith are cams 28, 28', whose function will be described in more detail below. It is to be understood that the pendulum arm 22 is rotationally fixed with respect to the pivot shaft portions 24, 24' and rotates in unison with the pivot shaft portions. The pivot shaft portions are supported on a pair of guide rollers such as illustrated at 30, 30' which are fixedly coupled to the pivot shaft portions.

FIG. 6 also illustrates the outer end of the support arm 18. The support arm 18 defines a pair of guide slots 32, 32' extending in a generally vertical direction. When assembled, the pivot shaft portions 24, 24' extend respectively through the slots 32, 32', with the guide rollers on the outside of the support arm and constrained by guide bars described below. This configuration defines an amount of vertical movement of the pivot shaft portions and pendulum arm with respect to the support arm 18.

Also affixed to the support arm 18 are two pair of guide bars, 34, 34', respectively flanking the guide slots. Additionally, the support arm 18 bears a pair of opposingly aligned lift rollers, one of which is indicated at 36 and which extend inwardly with respect to the support arm structure just below the guide slots 32, 32'.

When the pendulum arm and its attached pivot shaft portions 24, 24' are inserted into the guide slots 32, 32' of the support arm 18, the cams 28, 28' bear upon the associated lift rollers 36, 36'. The guide rollers 30, 30' ride between the respective pairs of guide bars 34 and restrict the pendulum arm 22 to two degrees of freedom of motion, one being vertical movement over the path defined by the guide slots 32, 32', and the other being rotative motion about a substantially horizontal axis.

As the cams bear against the associated lift rollers, and as the pendulum arm 22 rotates, the pendulum arm pivot is forced to translate along the path defined by the guide bars 34, 34'. The rate of translation with respect to rotational motion is a function of the cam design.

Figure 7:
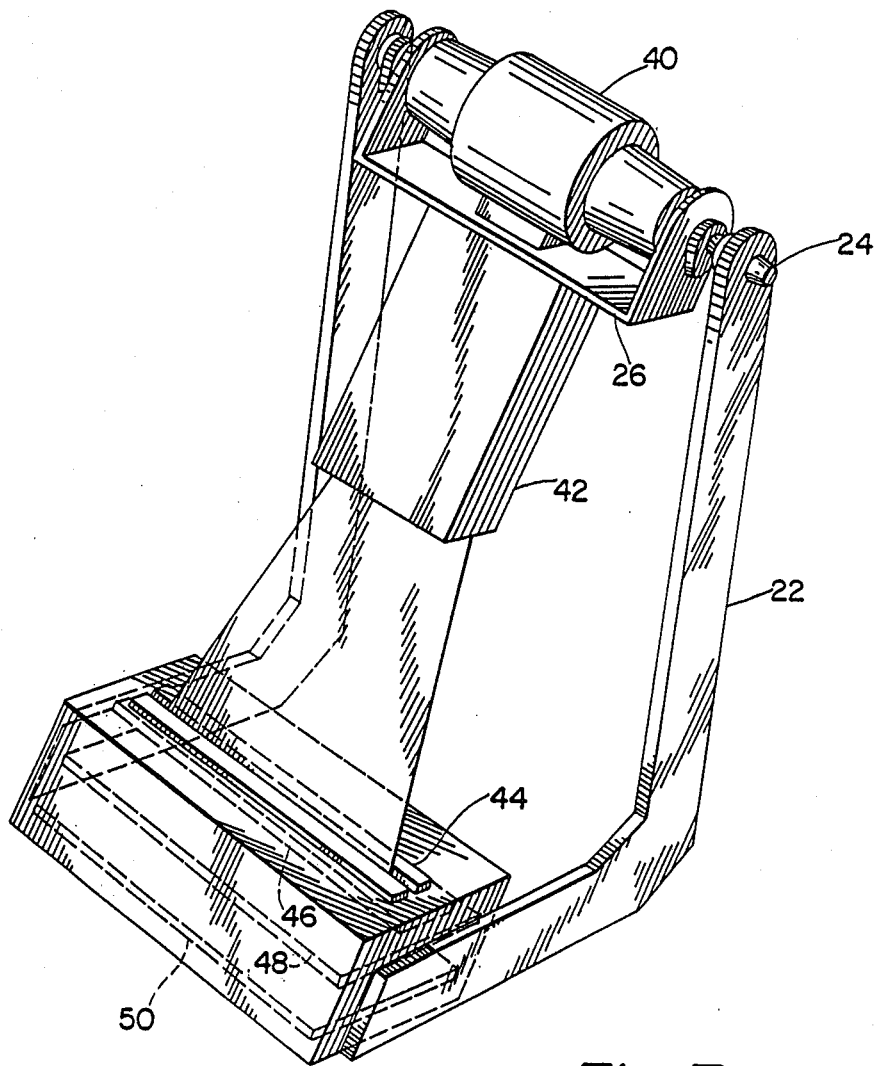
FIG. 7 is a detail drawing illustrating another portion of the system of FIGS. 1-4.
Figure 8:
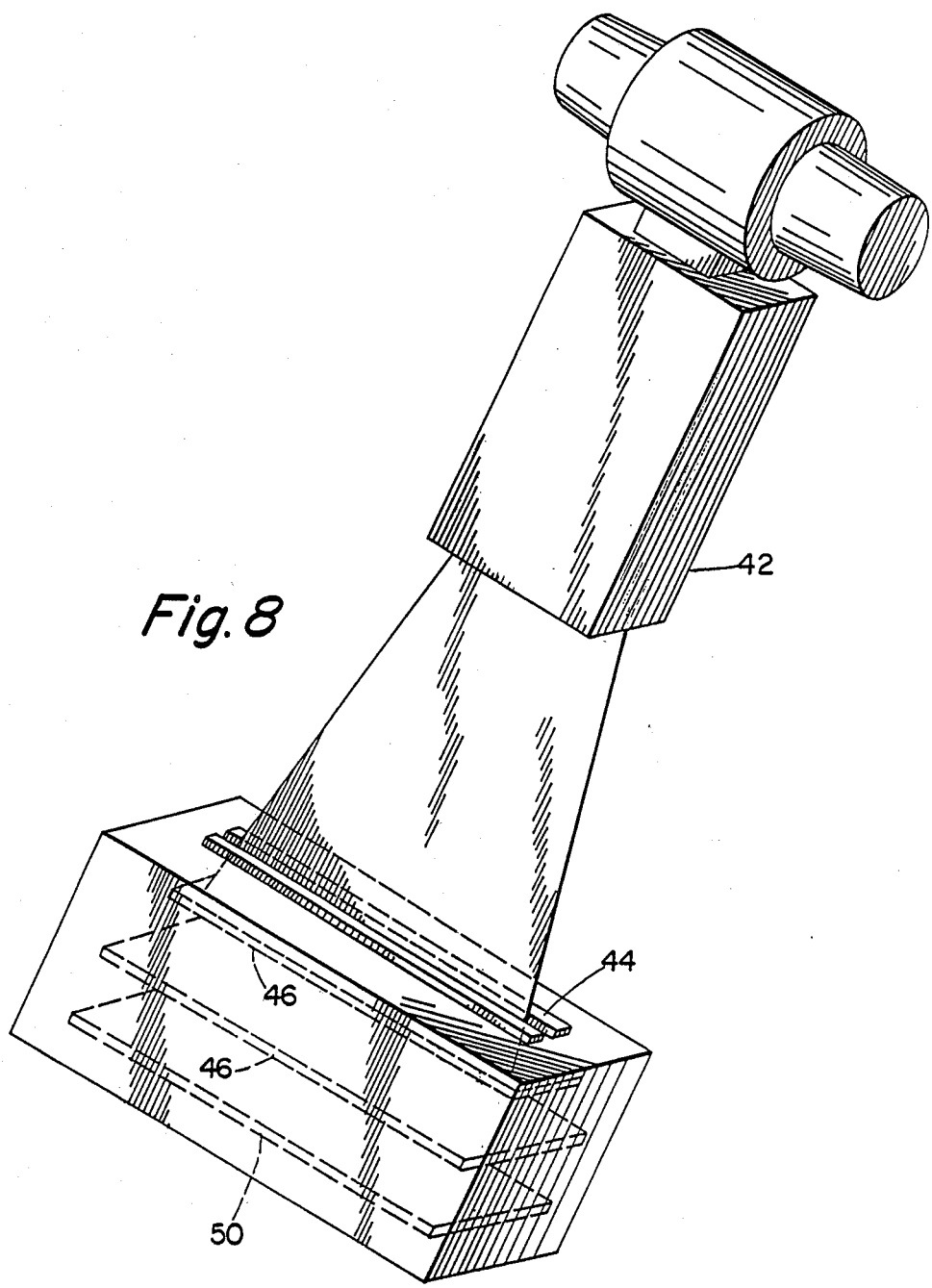
FIG. 8 is a detailed drawing illustrating in more detail the portion of the system shown in FIG. 7.

The pendulum arm 22 supports an imaging chain, as illustrated in FIGS. 7 and 8.

As previously stated, the imaging chain used in this radiation scanner system is based on slit scanning digital radiographic technology of known type.

Referring to FIGS. 7 and 8, there is illustrated an x-ray tube 40 of known variety for providing a source of radiation which is propagated through a patient to emerge therefrom in a pattern bearing information representing the internal structure or condition of the patient's body. A foreslit collimator 42 is generally aligned with the output of x-rays from the tube 40. An aft slot collimator 44 is also provided for collimating x-ray energy following its emergence from the subject, which subject is positioned during a study between the foreslit collimator 42 and the aft collimator 44.

Aligned with the aft slot collimator 44 is an image receptor 46. The x-ray tube, foreslit collimator, aft slot collimator and image receptor are rigidly coupled to the pendulum arm 22 and aligned such that an x-ray spread beam emitted from the foreslit collimator passes through the slot in the aft slot collimator and falls upon the image receptor 46.

The image receptor comprises a linear array of silicon photodiodes. This array can have one of a range of detector-to-detector spacing or "pitches" ranging from about 0.25 millimeters to about 2.0 millimeters. Lying on top of the photodiode array in the path of incident x-rays is an x-ray scintillator which converts incident x-ray photon energy to light photon energy. The light photon energy is detected by the individual photodiodes which comprise the photodiode array. Details of making and using such an image receptor are known in prior art literature, such as in the above referenced patent applications to Barnes, which are hereby expressly incorporated by reference.

The individual photodiodes of the image receptor 46 each produce an analog current which is a function of the incident light photon energy which it respectively detects. This analog current is converted to an analog voltage. Acquisition electronics, depicted at 48, are provided for processing the analog currents produced by the photodiodes. The photodiode signals are sampled by the acquisition electronics and evaluated. Current is converted to voltage, which is then amplified and converted from analog (image) information into digital information using appropriate known analog-to-digital conversion means.

A series of data buffers, multiplexers, and dedicated processing electronics, together referred to at reference character 50, are used to prepare the data acquired by the image receptor for transfer to storage, display, or recording devices in the form of known digital image and control data. Details of the data acquisition and electronics processes are described in prior art literature, such as the following, expressly incorporated by reference: Capp, M. P. et al, "Photoelectronic Radiology Department" S.P.I.E. Vol. 314, Digital Radiography 1981, pp. 2–7.

Connected to the imaging chain is a set of leads (not shown) over which digital image and control data is passed to devices of known type, such as located in the console 4, which convert this data into viewable medical diagnostic x-ray images presented on monitors. For the system of this invention, the imaging chain is connected to CRT displays, such as at 8 and in the console, and to hard copy recorders which produce x-ray films. These devices are of known type.

As set forth in more detail below, mathematical expressions have been developed which enable the calculation of the profile of the cams 28, 28' such that the rate of change of the gravitational potential energy of the pendulum arm, together with that of the imaging chain the arm carries, with respect to arm angular displacement, is nearly a constant throughout the scanning range. The rotational degree of freedom afforded the pendulum arm 22 allows the arm and the image chain to swing freely in a curved path which facilitates the scanning of patients with the x-ray spread beam and the associated downstream elements of the imaging chain. The cam is designed to allow for only a small net force which tends to move the arm from a position displaced from an equilibrim position toward the equilibrium position.

It can be seen that, when the pendulum arm is displaced from its at rest equilibrium position, and subsequently released, the force of gravity, without intervention by any electromechanical power means, causes the pendulum arm and the associated elements of the image chain to scan in a rotational direction. Because the pendulum and imaging chain can rotate freely in the compounding pendulum fashion described above, the potential energy of these components which rotate in unison would normally go from a maximum at the beginning of the swing, to zero at the point where its center of mass passes through a vertical line extending through the pivot shaft axis, and back to a maximum at the end of the swing (with some frictional losses, of course). During the same time the kinetic energy of the scanner assembly would respectively go from zero at the start, to a maximum when the center of mass passes the vertical center line through the pivot axis, and back to zero at the end of the swing (again, with some frictional losses).

It is desirable to regulate or modify the angular velocity of this gravity scanning from the simple pendulum motion described above. If one were to employ a free swinging pendulum, it would be impractical to use it to scan patients with an x-ray spread beam imaging system and with electronic imaging architecture developed for other known forms of slit projection radiography. The speed of scanning, particularly at the bottom of its arc, would be excessively fast and would impose an unacceptable design complexity on the acquisition electronics and system architecture used in those systems. The design of electronics for processing data at rates generated during the most rapid portion of the scanning cycle would result in a system which would be prohibitive in cost and unduly complicated.

To alleviate this problem, this invention preferably employs scan velocity regulating apparatus and technique described generally above in connection with FIGS. 7 and 8, and described in more detail below.

Figure 6A:
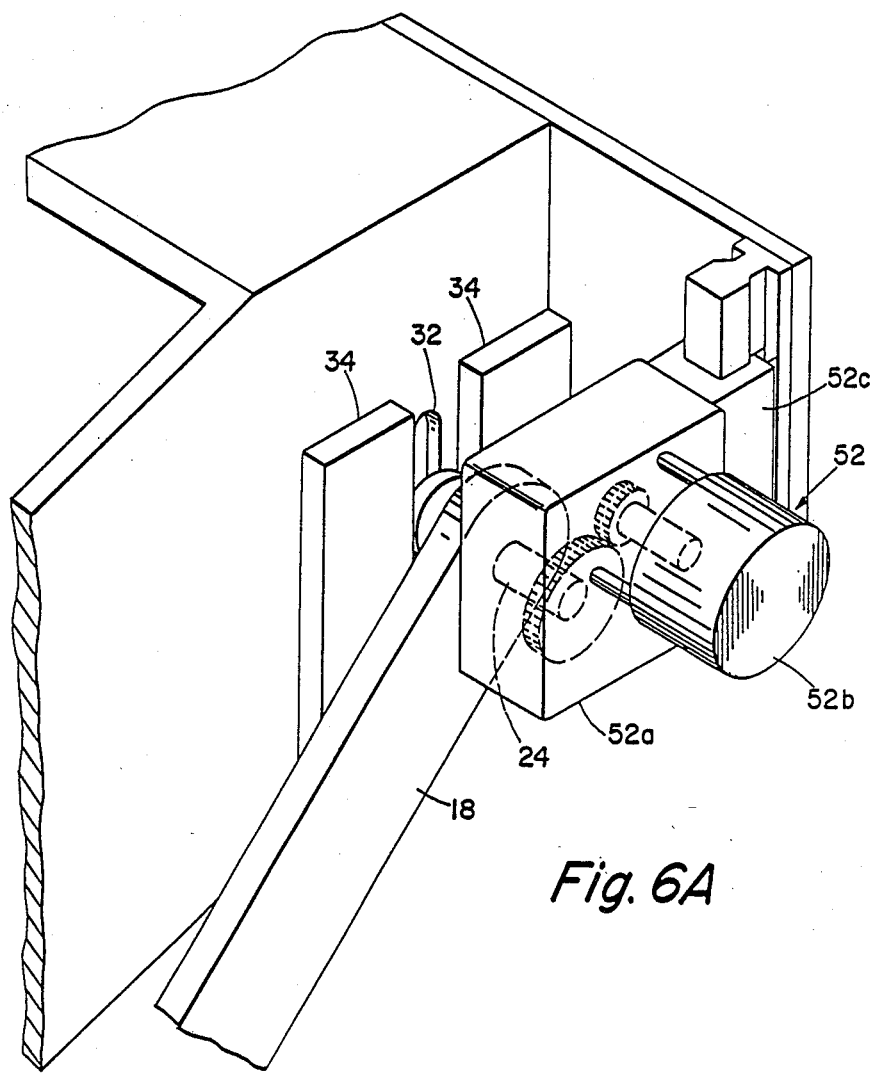
FIG. 6A is a detail drawing showing another portion of the system of FIGS. 1-6.

As mentioned above, the primary component for implementing scan speed regulation are the cams 28, 28' and their specific design. Stated generally, the cams are designed such that the center of mass of the combined pendulum arm and imaging chain with which it moves falls, as the detector rotates downwardly, in a manner controlled by the design of the cams. The cams are preferably designed so that the rate of change of the gravitational potential energy of the combined pendulum arm and image chain, with respect to scan angle, is nearly constant. The result of these design parameters is that, in effect, a constant driving torque is applied to the combined pendulum arm and fixedly attached image chain assembly, here collectively called the "scanner assembly". This condition would normally result in constant angular acceleration of the scanner assembly. But because the angular acceleration of the scanner assembly is constant, and not sinusoidal, as it would be for a normal simple pendulum motion, a constant friction brake of clutch, such as shown at 52 (FIG. 6A), can be applied to the pivot shaft portions 24, 24', to regulate angular velocity of the scanner assembly. It has been shown that, by the use of the design set forth herein, one can maintain the angular velocity of the scanner assembly to within about 20% of a nominal, predetermined desired scan velocity.

Details of the friction brake assembly can easily be provided by one of ordinary skill in the art. However, for the benefit of those who may not be intimately conversant with this art, a description of the brake 52 follows:

The brake assembly includes a speed-increasing gearbox 52a and a brake subassembly 52b. The input shaft of the gearbox is rigidly attached to one of the pivot shaft portions 24, 24'. The gearbox itself is supported by the pivot shaft and "floats" up and down as the cams lift and lower the pivot shaft. The gearbox is further supported and kept from rotating by a linear bearing 52c. The output shaft of the gearbox is rigidly coupled to the brake subassembly 52b. The brake subassembly is supported by attachment to the gearbox housing.

Embodiments of the brake subassembly are commercially available. Its basic operating characteristic is that it resists rotation of its shaft. A suitable brake subassembly is a Model ECG-1 Brake sold under the trade-mark "PERMA-TORK", and manufactured and sold by Dana Corporation, Toledo, Ohio, USA.

The brake function can be expressed mathematically:

$$L' = f(w') \tag{B1}$$

where $L'$ is the braking torque at the shaft, $w'$ is the angular speed of the shaft, and $f()$ is some function which is dependent on the nature of the brake. For example, there are commercially available brakes, called permanent magnet eddy current brakes, which have a linear speed/torque function:

$$L' = s\,w' \tag{B2}$$

where s is a constant.

The gearbox has a gear ratio G and satifies the following equation:

$$w' = Gw \tag{B3}$$

where w and w' are the angular speeds of the input and output shafts, respectively.

The power that the brake must dissipate is given by k in equation (8) below. Power is given by torque times angular speed, and so:

$$k = L'\,w' \tag{B4}$$

In the case of a linear speed/torque function, for example:

$$k = s(w')^2 = s(Gw)^2 \tag{B5}$$

Equation (8) then implies:

$$sG^2 = mgb\,\sin(\alpha)w. \tag{B6}$$

This is the design equation for the gearbox/brake assembly for a linear brake.

To demonstrate how to use equation (B6), consider the following example. Suppose we choose a linear permanent magnet eddy current brake with 1 mN torque at 10 rad/s angular speed. Then:

$$s = (1\ mN)/(10\ rad/s). \tag{B7}$$

$$\begin{aligned}
b &= .8\ m \\
c &= 1.0\ m \\
\alpha &= 25° \\
m &= 110\ kg \\
w &= 0.1\ rad/s \\
s &= 0.1\ mNs \\
g &= 9.8\ m/s^2
\end{aligned} \tag{B8}$$

Then equation (B6) implies a gear ratio G of 191.

Many advantages ensue from the use of the herein described scanner apparatus employing gravity powered pivotal scanning and scan velocity regulation. The system is entirely passively mechanical in nature, requiring relatively few parts and no positive power drive to effect scanning. The system is simple, reliable and inexpensive to produce. The mechanism employing the cam 28 forces the scanner assembly to raise its own mass as it rotates under the power of gravity, which effectively permits the scan velocity to be regulated to within about 20% of a nominal value. It has been shown that the presently described mechanism provides adequate regulation of scan velocity, while adding only a minimum amount of mass to the system. This advantage is particularly important when designing portably deployable military or commercial x-ray systems.

Figure 9:
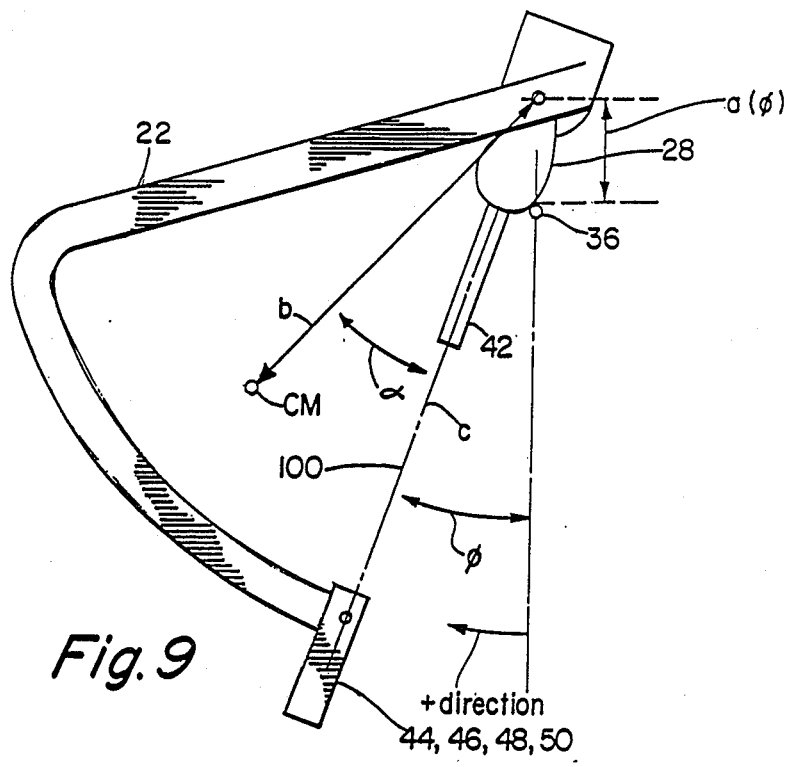
FIG. 9 is a diagram illustrating geometrical relationship among various portions of the system illustrated in FIGS. 1-8.

Mathematical derivation for system parameters will now be discussed. To do this, certain definitions should be stated at the outset:

DEFINITIONS (See FIG. 9)

Call the line 100 connecting the detector and pivot axis the central ray.

CM = center of mass of scanner assembly
$\alpha$ = angle between central ray and pivot/CM line
$\phi$ = between central ray and vertical
$w = \frac{d\phi}{dt}$ = angular scan speed
$a(\phi)$ = distance from (top of) lift roller to pivot
b = distance from CM to pivot
c = distance from pivot to detector
m = mass of scanner assembly
g = acceleration due to gravity
V = gravitational potential energy of scanner assembly
T = kinetic energy of scanner assembly
H = heat energy dissipated into a friction clutch acting at the pivot
y = vertical position of detector with respect to its position when $\phi = 0$
x = horizontal position of detector with respect to its position when $\phi = 0$
$I_{cm}$ = moments of inertia of scanner assembly about CM
k = power dissipated in the brake at scan speed W.

ANALYSIS

Conservation of energy requires:

$$\frac{dT}{dt} + \frac{dV}{dt} + \frac{dH}{dt} = 0. \tag{1}$$

The friction clutch acts at the scanner pivot and dissipates energy at a rate which depends on scan speed. Equation (1) implies:

$$\frac{dV}{dt} = -\frac{dH}{dt} \quad (2)$$

where the assumption has been made that $$\frac{dT}{dt}$$

is negligible compared to $$\frac{dV}{dt}.$$

This assumption is justified below.

If we impose the constraint of constant scan speed, Eq. (2) implies:

$$\frac{dV}{d\phi} = \frac{k}{w}, \quad (3)$$

where k is the power dissipated in the brake and w is angular scan speed. Both k and w are positive constants.

The gravitational potential energy of the scanner assembly may be written:

$$V(\phi) = mg \{a(\phi) - a(0) - b \cos(\phi + \alpha) = b \cos(\alpha)\}, \quad (4)$$

where the expression in braces is the vertical position of the CM with respect to its location when $\phi=0$. The function a ($\phi$) defines the shape of the cam 28.

Equations (3) and (4) imply $$\frac{da}{d\phi} = -b \sin(\phi + \alpha) + \frac{k}{mgw}, \quad (5)$$

which can be integrated to give $$a(\phi) = a(o) + b \cos(\phi + \alpha) - b \cos(\alpha) + \frac{k\phi}{mgw}. \quad (6)$$

Equation (6) contains one free parameter, the brake constant k. For a practical scanner system, $a(\phi)-a(0)$ should be (at least approximately) symmetrical about $\phi=0$.

What value shall k have in order to make $a(\phi)-a(0)$ as symmetrical as possible? To second order in $\phi$, Eq. (6) may be written:

$$a(\phi) - a(0) \simeq \left\{ \frac{k}{mgw} - b \sin(\alpha) \right\}\phi - \frac{1}{2} b \cos(\alpha) \phi^2. \quad (7)$$

The $\phi$ term is eliminated if $$k = (mgwb) \sin(\alpha), \quad (8)$$

thereby making $a(\phi)-a(0)$ approximately symmetrical.

Equations (6) and (8) imply $$a(\phi) = a(0) + b \{\sin(\alpha)\phi + \cos(\phi + \alpha) - \cos(\alpha)\}. \quad (9)$$

Equation (9) is the design equation for each cam, while equation (8) defines the power dissipation required of the brake at angular speed w.

CAM DESIGN AND DETECTOR PATH

Figure 10:
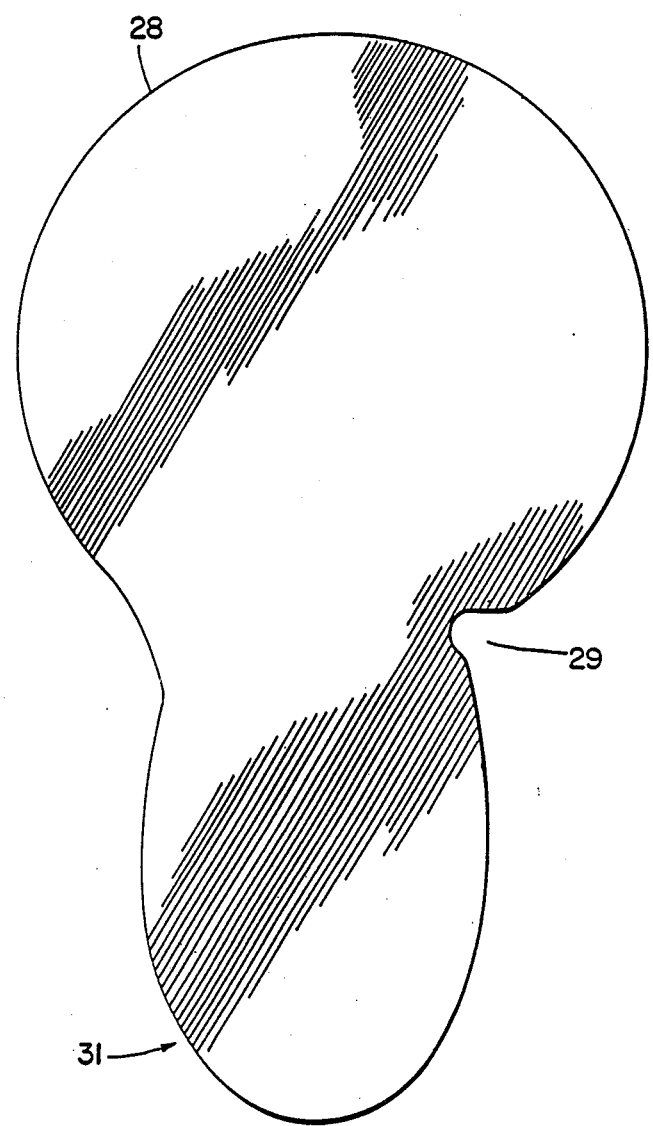
FIG. 10 is a diagram illustrating the actual geometrical shape of a cam incorporated into the system of FIGS. 1-9.

A practical scanner system with a steel scanner assembly will have (approximately) the following parameters:

$$\begin{aligned} b &= 0.8 \text{ m} \\ c &= 1.0 \text{ m} \\ \alpha &= 25 \text{ deg.} \\ m &= 110 \text{ kg} \\ w &= 0.1 \text{ rad/s,} \end{aligned} \quad (10)$$

with a scan angle from $\phi \simeq +20$ degrees to $\phi \simeq -20$ degrees. A full scale cam design for this scanner with a (0)=0.127 m (5 inches) is plotted in FIG. 10. Note that an indented, or detent, portion 29 of the cam provides a stable "locked" position before a scan is initiated. A scan may be initiated by simply giving the scanner assembly a push. A "tail" portion 31 on the cam stops the scan. Once a scan is over, the scanner assembly can be manually reset to its pre-scan cocked or park position.

Figure 11:
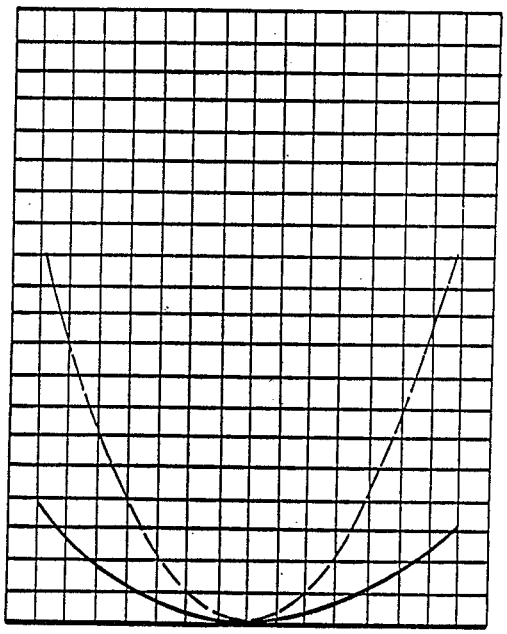
FIG. 11 is a graphical plot of motion of a component of the system of FIGS. 1-8.

The actual path traversed by the detector is plotted in the solid line shown in FIG. 11. The equations for this motion are $$\begin{aligned} x &= c \sin(\phi) \\ y &= a(\phi) - a(0) + c[1 - \cos(\phi)]. \end{aligned} \quad (11)$$

Values of $\phi$, x and y are tabulated in Table 1, where it is apparent that the motion is nearly horizontal from $\phi \simeq +20$ degrees to $\phi \simeq -20$ degrees. The detector path is illustrated in the solid line of FIG. 11. Thus, the cam/brake design not only provides approximately constant angular scan speed, but also a nearly horizontal detector path.

It should be noted that in FIG. 11, the vertical axis scale is double that of the horizontal axis. Thus, the dotted curve actually corresponds to an arc, and the solid line, corresponding to the detector path of the present embodiment, is nearly horizontal between $-20°$ and $+20°$.

The justification for the assumption that $$\frac{dT}{dt}$$

is negligible compared to $$\frac{dT}{dt}$$

is as follows:

Demonstration that $\frac{dT}{dt} << \frac{dV}{dt}$

The kinetic energy of the scanner assembly can be written:

$$T = \frac{1}{2} m w^2 \left( \frac{Icm}{m} + b^2 - 2bc \sin(\phi)\sin(\phi + \alpha) + \quad (A1) \right.$$

-continued $$c^2 \sin^2(\phi) \Bigg),$$

which yields:

$$\frac{dT}{dt} = -mbcw^3 \Bigg\{ \cos(\phi)\sin(\phi+\alpha) + \quad (A2)$$

$$\sin(\phi)\cos(\phi+\alpha) - \frac{c}{b}\sin(\phi)\cos(\phi) \Bigg\}.$$

The expression in brackets is of order unity, so $$\left|\frac{dT}{dt}\right| \approx mbcw^3. \quad (A3)$$

Equation (3) and (8) imply $$\frac{dV}{dt} = mgwb \sin(\alpha). \quad (A4)$$

Hence, $$\frac{\left|\frac{dT}{dt}\right|}{\left|\frac{dV}{dt}\right|} = \frac{cw^2}{g\sin(\alpha)}, \quad (A5)$$

and, using the values in Equation (10), $$\frac{\left|\frac{dT}{dt}\right|}{\left|\frac{dV}{dt}\right|} = 0.0024. \quad (A6)$$

TABLE 1

| φ | x | (with cam) y | (without cam) y |
|---|---|---|---|
| 25 deg | .423 m | .030 m | .094 m |
| 20 | .342 | .019 | .060 |
| 15 | .259 | .010 | .034 |
| 10 | .174 | .004 | .015 |
| 5 | .087 | .001 | .004 |
| 0 | 0 | 0 | 0 |
| −5 | −.087 | .001 | .004 |
| −10 | −.174 | .004 | .015 |
| −15 | −.259 | .008 | .034 |
| −20 | −.342 | .014 | .060 |
| −25 | −.423 | .021 | .094 |

These values are illustrated graphically in FIG. 11.

It is to be understood that this disclosure is intended as illustrative, rather than exhaustive, of the present invention. Those of skill in the art may be able to make additions or modifications to, or deletions from, the disclosed embodiment, without departing from the spirit or scope of the invention, as set forth in the following claims:

We claim:

1. A radiographic imaging scanner system comprising:
   (a) a source of propagating penetrative radiation through a portion of a subject to emerge therefrom in a pattern;
   (b) a radiation detector spaced from the source and positioned to receive said pattern of radiation;
   (c) means for mounting said detector for gravity powered scanning movement including both rotational and translational movement during radiation production along a path defining a curved line substantially in a vertical plane;
   (d) means for regulating gravitational potential energy of said detector to fall at a rate during said gravity powered scanning movement to cause application of substantially uniform torque to effect said rotational movement over a predetermined angular displacement;
   (e) means associated with said detector for producing an image representing said received radiation.

2. The system of claim 1, wherein said mounting means comprises:
   (a) an arm mounted for pivotal movement about a substantially horizontal axis; and
   (b) means for mounting said source and said detector for movement with said arm.

3. The system of claim 1, further comprising:
   brake means for continuously regulating velocity of said scanning movement.

4. The system of claim 2, wherein:
   said mounting means comprises means for facilitating said gravity powered scanning motion substantially independent of other power.

5. The system of claim 4, wherein said motion facilitating means comprises said mounting means having a tower member and said arm being mounted on said tower member in pendulum fashion.

6. A radiation scanner system comprising:
   (a) a support structure pivotally mounted to a support for angular gravity powered motion as a pendulum;
   (b) a source of penetrative radiation
   (c) a detector mounted on said support structure and being spaced from said source to accommodate placement of a subject there between;
   (d) mechanical lift mechanism coupled between said support structure and said support for changing the elevation of said support structure as a function of rotational pivotal angular displacement of said support structure for causing potential energy of said detector and said support during pivotal motion to vary as a substantially linear function of angular displacement of said detector; and
   (e) means associated with the detector for producing an image corresponding to radiation incident on said detector.

7. The system of claim 6, wherein said mechanical lift mechanism comprises a cam and lift roller assembly.

8. A radiation scanner system comprising:
   (a) a source of penetrative radiation;
   (b) a radiation detector;
   (c) means for mounting said radiation detector for gravity powered rotational movement along a path;
   (d) an electromechanical brake for continuously applying braking force inhibiting and dissipating energy of said gravity powered rotational movement over substantially the entire course of said movement; and (e) means associated with the detector for producing a representation in response to receipt of radiation by said detector.

9. The system of claim 8, wherein said path defines a vertical component.

10. The system of claim 8, further comprising: means for regulating the velocity of said gravity powered rotational movement.

11. The system of claim 10, wherein said means for regulating velocity comprises a lift mechanism.

12. The system of claim 11, where:
(a) said gravity-responsive movement has downward component, and
(b) said velocity regulating means comprises means for elevating the center of mass of a portion of said system in response to said detector's motion.

13. The system of claim 12, wherein said elevating means comprises a mechanism including a cam.

14. A radiation scanner system comprising:
(a) a source of penetrative radiation;
(b) a radiation detector comprising part of an assembly and being mounted for gravity powered pivotal movement about a pivot axis;
(c) means proximate the pivot axis for changing the elevation of the center of mass of at least a portion of said assembly in response to detector pivotal movement to maintain the rate of change of gravitational potential energy of said assembly as a substantially linear function of detector angular displacement during said gravity powered pivotal movement, and
(d) means associated with the detector for producing a representation in response to receipt of radiation by detector.

15. A radiation scanner system comprising:
(a) a base;
(b) a tower member extending generally vertically and mounted to said base;
(c) an arm;
(d) means for pivotally mounting said arm to said tower member to provide gravity powered rotation about a substantially horizontal axis;
(e) at least a portion of an imaging chain mounted on said arm, said portion including at least a radiation detector;
(f) a source of penetrative radiation defining a focal spot and located such that said detector, in response to pivoting movement of said arm, rotates about said focal spot;
(g) guide apparatus coupled between said arm and said tower member for defining a path of translational movement for said arm having a vertical component;
(h) a lift member mounted fixed with respect to one of said tower member and said arm;
(i) a cam mounted fixed with respect to the other of said tower member and said arm and positioned to engage said lift member to apply force to change the vertical elevation of the center of mass of a portion of said arm in response to pivotal movement of said arm with respect to its said pivot axis; and
(j) means associated with said detector for producing a representation in response to receipt of radiation by the detector.

16. The system of claim 15, wherein said cam defines a detent portion for holding said detector in a predetermined position in response to movement of said detector to said position.

17. A radiographic projection scanning imaging method comprising the steps of:
(a) propagating penetrative radiation through a portion of a subject to emerge therefrom in a pattern;
(b) detecting radiation of said pattern by use of a radiation detector spaced from the source, said detector being pivotally movable;
(c) displacing said detector from a position of stable equilibrium to an unstable position for facilitating pivotal movement of said detector by the force of gravity toward a stable equilibrium position for scanning along a path located in a substantially vertical plane; and
(d) changing the elevation of the pivot axis of said detector motion as a function of detector angular displacement;
(e) continuously braking said rotational movement; over substantially the entire course of said movement, and
(f) producing an image representing said detected radiation.

18. The method of claim 17, wherein said detector is mounted as a portion of an assembly comprising an arm, said step of moving said detector comprising:
pivotally moving said arm about a substantially horizontal axis.

19. The method of claim 17, wherein said braking step comprises the step of:
adjustably and substantially continuously regulating velocity of said scanning movement.

20. The method of claim 17, wherein said step of moving said detector comprises facilitating gravity responsive movement substantially independently of other power.

21. A radiation scanning method utilizing a system including a source of penetrative radiation and a radiation detector, said method comprising the steps of:
(a) actuating the radiation source to propagate penetrative radiation toward the detector;
(b) facilitating gravity powered movement of said detector substantially independently of the application of other power for effecting such movement, said movement comprising:
(i) rotational movement having a vertical component, and
(ii) translational movement having a vertical component opposite said rotational movement vertical component superimposed on said rotational movement in an amount to cause detector potential energy to decrease as a substantially linear function of detector angular displacement; and
(c) producing a representation of an image in response to receipt of radiation by said detector.

22. The method of claim 21, further comprising the step of:
adjustably regulating the velocity of said gravity responsive movement over a continuous range of movement.

23. The method of claim 22, wherein said regulation step comprises mechanical regulation.

24. A radiation scanning method utilizing a source of penetrative radiation and a radiation detector, the detector including part of an assembly, the assembly being mounted for pivotal movement about an axis and, along a path having a vertical component, said method comprising the steps of:

(a) actuating said source to propagate penetrative radiation toward the detector;

(b) moving said detector along said path during said actuation, by effecting pivotal motion of said assembly about said pivot axis;

(c) changing the elevation of the center of mass of the assembly to maintain the rate of change of the gravitational potential energy of said assembly at an approximately uniform non-zero value over a range of detector angular movement, and (d) producing a representation in response to receipt of radiation by the said detector.

25. A radiation scanner system comprising:
(a) a penetrative radiation source;
(b) a support structure;
(c) a radiation detector;
(d) connecting structure coupled to said detector and to said support structure for holding said detector spaced from said source to receive penetrative radiation therefrom, said connecting structure being mounted to said support structure for pivotal movement of said connecting structure and said detector about a pivot axis;
(e) lift mechanism coupled between said connecting structure and said support structure for changing elevation of said connecting structure as a function of angular location of said connecting structure and said detector about said pivot axis, and to maintain system potential energy as a substantially linear function having non-zero slope, with respect to detector angular displacement; and
(f) means associated with said detector for producing a representation of penetrative radiation received by said detector.

26. The system of claim 26, further comprising:
brake mechanism for applying braking force tending to inhibit said pivotal movement.

27. The system of claim 26, where:
said brake mechanism comprises an adjustable electromechanical brake.

28. The system of claim 25, wherein:
said lift mechanism comprises a roller cam lift apparatus.

29. A radiation scanner system comprising:
(a) a support structure;
(b) a connecting element coupled to said support structure for gravity powered pivotal movement about a pivot axis;
(c) a penetrative radiation source coupled to said connecting element;
(d) a penetrative radiation detector coupled to said connecting element and spaced from the source said source and detector being arranged on said connecting element to enable said gravity powered pivotal movement of said source and detector;
(e) lift apparatus coupled between the connecting element and the support structure for changing the elevation of said pivot axis during and as a function of said gravity powered pivotal movement of the connecting element to cause the path of the detector during said pivotal movement to assume a nearly linear configuration, and
(f) means associated with the detector for producing a representation of radiation incident on said detector.

30. A radiation scanner comprising:
(a) a support structure;

(b) a connecting element coupled to the support structure and including means facilitating gravity powered pivotal movement of said connecting element about a pivot axis;
(c) a penetrative radiation detector coupled to the connecting element;
(d) a penetration source coupled to the connecting element and spaced from the source;
(e) lift apparatus coupled between the connecting element and the support structure for altering the elevation of said connecting element and detector combination in response to pivotal movement of the detector, such that the resultant motion of said detector follows a nearly linear path during a portion of said pivotal movement of said detector about said pivot axis; and,
(f) means associated with the detector for producing a representation of radiation incident on said detector.

31. A radiation scanner system comprising:
(a) a support structure;
(b) a connecting element coupled to said support structure for pivotal movement about a pivot axis;
(c) a penetrative radiation source connected to said connecting element;
(d) a penetrative radiation detector coupled to said connecting element and spaced from the source, the respective placement of said source and detector on said connecting element providing for gravity induced pivotal movement of said detector over a portion of the range of said pivotal movement such that, over said range, the effect of pivotal motion of said detector tends to lower the elevation of said detector;
(e) lift structure coupled between said connecting element and said support structure for raising the elevation of said pivot axis during said downward tending pivotal movement of said detector such that, over a range of said gravity induced pivotal movement, gravity induced torque tending to rotate the connecting element, source and detector is approximately uniform; and
(f) means associated with said detector for providing a representation of radiation incident on said detector.

32. The system of claim 31, further comprising;
a brake for continuously inhibiting said pivotal movement over a substantial range of said pivotal movement.

33. The system of claim 32, wherein:
said brake comprises an electromechanical brake means.

34. The system of claim 32, wherein said brake comprises:
a dynamic brake.

35. The system of claim 32, wherein said radiation scanner system further comprises:
a brake having a substantially uniform angular speed to torque ratio.

36. A radiation scanner system comprising:
(a) a support structure;
(b) a connecting element coupled to said support structure for pivotal motion about a substantially horizontal pivot axis;
(c) a penetrative radiation source connected to said connecting element
(d) a penetrative radiation detector connected to said connecting element and spaced from the source, the arrangement of the source and detector being such that, during a portion of pivotal movement, said detector is lowered.
(e) lift apparatus coupled between the connecting element and the support structure for elevating said pivot axis during downward movement of said detector resulting from said pivotal movement, said lift apparatus tending to stabilize detector velocity during said pivotal motion and tending to flatten toward the linear detector movement during said pivotal motion, by both linearizing the rate of decrease of potential energy of the connecting element, source and detector during a portion of said pivotal motion and by at the same time introducing eccentricity into the detector path of motion;
(f) a brake applicable for continuously inhibiting said pivotal motion over a substantial detector angular displacement; and
(g) means associated with the detector for producing a representation of radiation incident on the detector.

37. A radiation scanner system comprising:
(a) a support structure;
(b) a connecting element coupled to the support structure for gravity powered pivotal movement about a substantially horizontal pivot axis;
(c) a penetrative radiation source coupled to said connecting element;
(d) a penetrative radiation detector coupled to said connecting element and spaced from the source, said detector tending to trace an arcuate path during said pivotal movement, said path having a uniform radius of curvature with respect to said pivot axis;
(e) lift means coupled between the connecting element and the support structure for altering the elevation of said pivot axis such that the elevation of said detector is maintained within a range substantial narrower than a range without said pivot axis elevation alteration;
(f) said lift means additionally for regulating the angular acceleration of said connecting element to a substantially constant value; and
(g) brake means for regulating detector velocity to within a narrow range of a predetermined velocity.

38. A radiation scanner system comprising:
(a) a support structure;
(b) a connecting element coupled to the support structure for gravity powered pivotal movement about a substantially horizontal pivot axis;
(c) a penetrative radiation source coupled to said connecting element;
(d) a penetrative radiation detector coupled to said connecting element and spaced from the source, said detector tracing an arcuate path during said pivotal movement, said path having a uniform radius of curvature with respect to said pivot axis;
(e) means coupled between the connecting element and the support structure for superimposing transnational movement having a vertical component on said gravity powered pivotal movement to cause said detector path to flatten, and to maintain the angular acceleration of said connecting element to a substantially constant value; and
(f) means operating on said connecting element to regularize detector velocity.

39. A radiation scanner system comprising:
(a) a support structure;
(b) a connecting element coupled to the support structure for gravity powered pivotal movement about a substantially horizontal pivot axis;
(c) a penetrative radiation source coupled to said connecting element proximate the pivot axis;
(d) a penetrative radiation detector coupled to said connecting element and spaced from the source and pivot axis for movement along a path during said gravity powered pivotal movement of said connecting element, the arrangement of the source and detector on the connecting element relative to the pivot axis enabling said gravity powered pivotal movement;
(e) means coupled to the connecting element to cause a flattening of the detector path; and
(f) means coupled to the connecting element to cause a stabilization of detector velocity during pivotal movement of said connecting element.

40. A radiographic projection scanner comprising:
(a) a support structure;
(b) a connecting element;
(c) mounting means coupling said connecting element to said support structure for pivotal movement about a pivot axis;
(d) a penetrative radiation source coupled to said connecting element;
(e) a penetrative radiation detector coupled to said connecting element and spaced from said source, the arrangement of said source, detector element and connecting element with respect to the pivot axis enabling gravity powered pivotal motion of the combination of said source, connecting element and detector about said pivot axis;
(f) lift apparatus coupled between said connecting element and said support structure for altering the elevation of said pivot axis, and therefore of said connecting element combination, in response to said gravity powered pivotal movement of said detector, such that the resultant motion of said detector follows a nearly linear path during a portion of said pivotal movement of said detector about said pivot axis, and
(g) means associated with the detector for producing a representation of radiation incident on said detector.

41. A projection scanning imaging system utilizing penetrative radiation, said system comprising:
(a) a support structure;
(b) an assembly including:
 i. a connecting element;
 ii. a penetrative radiation source coupled to said connecting element, and
 iii. a penetrative radiation detector also coupled to said connecting element but spaced from said source;
(c) apparatus for coupling said assembly to said support structure for pivotal motion about a pivot axis;
(d) the components of said assembly being arranged such that the combined center of mass of said assembly is displaced substantially from said pivot axis, enabling gravity powered pivotal movement of said assembly;
(e) lift apparatus coupled between said assembly and said support structure for changing the elevation of said pivot axis as a function of said gravity powered pivotal movement of said assembly, and
(f) means coupled to said detector for producing an image in response to penetrative radiation incident upon said detector.

* * * * *